United States Patent [19]

Fukazawa et al.

[11] Patent Number: 5,338,745

[45] Date of Patent: Aug. 16, 1994

[54] AMIDE DERIVATIVES OF DIHYDROCAFFEIC ACID AND THEIR APPLICATION TO PHARMACEUTICALS

[75] Inventors: Nobuyuki Fukazawa; Hajime Iizuka; Osamu Yano, all of Mobara; Yukio Miyama, Chousei, all of Japan

[73] Assignee: Mitsui Toatsu Chemicals, Incorporation, Tokyo, Japan

[21] Appl. No.: 847,005

[22] PCT Filed: Aug. 8, 1991

[86] PCT No.: PCT/JP91/01063

§ 371 Date: Apr. 8, 1992

§ 102(e) Date: Apr. 8, 1992

[87] PCT Pub. No.: WO92/02490

PCT Pub. Date: Feb. 20, 1992

[30] Foreign Application Priority Data

Aug. 10, 1990 [JP] Japan .................. 2-210244

[51] Int. Cl.$^5$ .................. A61K 31/445; C07D 211/12; C07D 407/02

[52] U.S. Cl. .................. 514/330; 514/318; 514/321; 546/193; 546/197; 546/226

[58] Field of Search .................. 546/197, 226, 193; 514/321, 330, 318

[56] References Cited

FOREIGN PATENT DOCUMENTS

0399814A2 5/1990 European Pat. Off. .

OTHER PUBLICATIONS

Junard et al. "Long-term administration of mouse nerve growth faith to adult rats" CA 114:115710w (1990).

Fukazawa et al. "Preparation of catechol derivatives" CA 112(15) 138764q (1990).

Koul et al. "Synergists for pyrethrum" CA 92:123386n (1980).

Chemical Abstracts, vol. 87, No. 17, Oct. 1977, Columbus, Ohio, U.S. Abstract No. 134467n "Borohydride Reduction . . . Amines" p. 667.

Chemical Abstracts, vol. 92, No. 15, Apr. 1980 Columbus, Ohio, Abstract No. 123386n "Synergists for Pyrethrum . . . Acids" p. 215.

Chemical Absracts, vol. 105, No. 23, Dec. 1986 Columubs, Ohio, U.S. Abstract No. 202725n "Chemical Structure–Biological Activity . . . Analogs IV" p. 14.

Journal of the Chemical Society, Perkin Transactions 1 No. 6, (1983), Letchworth GB pp. 1219–1221 Sondengam et al. "Convenient Reduction . . . Couple".

Tetrahedron Letters No. 10, Mar. 1976, Oxford GB pp. 763–766 Umino et al. "Sodium Acyloxyborohydride as new Reducing Agents . . . Amines".

Journal of Chromatographic Science vol. 29, No. 6, Jun. 1991 pp. 267–271 Noggle et al. "Gas Chromatographic and Mass . . . Sassafras Oil".

Furukawa et al., FEBS 4216, vol. 208, No. 2 (Nov. 1986) "Aliphatic side chain of catecholamine potentiates the stimulatory effect of the catechol part on the synthesis of nerve growth factor" pp. 258–262.

Primary Examiner—Celia Chang
Attorney, Agent, or Firm—Nixon & Vanderhye

[57] ABSTRACT

Therapeutic agents for degressive diseases in the central nervous system, which contain amide derivatives of dihydrocaffeic acid of the general formula (I)

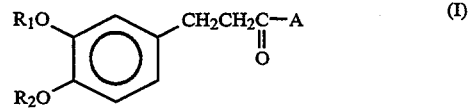

wherein, $R_1$ and $R_2$ and A are defined in the specification; the compounds exert a nerve growth factor inducing action and thus are effective for the prevention of the progression of degenerative diseases in the central nervous system and the therapeutic treatment thereof.

3 Claims, No Drawings

AMIDE DERIVATIVES OF DIHYDROCAFFEIC ACID AND THEIR APPLICATION TO PHARMACEUTICALS

BACKGROUND OF THE INVENTION

1. Field of the Invention

The present invention relates to amide derivatives of dihydrocaffeic acid and their application to pharmaceutical uses. More specifically, the present invention relates to amide derivatives of dihydrocaffeic acid which are capable of inducing production and secretion of a nerve growth factor (hereinafter referred to as NGF) in specific tissues in the brain and to pharmaceutical agents containing these derivatives as effective constituents for the prevention of the progression of degenerative diseases in the central nervous system and the therapeutic treatment thereof.

2. Description of the Prior Art

With extended average life expectancy, rapid progress in research has been made all over the world in order to establish methods for early diagnosis, ethiological study and therapeutic treatment of various gerontological diseases; degenerative diseases in the central nervous system are a major object of this research. In particular, senile dementia of Alzheimer type (hereinafter abbreviated to as SDAT), a typical disease of such diseases, is now becoming a big social problem because the number of the cases is markedly increasing, mainly in developed countries, and the patients suffer through a miserable progressive course. Although many researchers and clinicians have been intensively studying the pathology of this disease, particularly in recent years, the fundamental cause of the disease has not been elucidated and therefore no effective methods for the early diagnosis and treatment of the disease have been established.

However, a number of pathological observations demonstrates that the direct causes of the early characteristic symptoms of SDAT, such as memory failure and disorientation, are the progressive changes in large cell cholinergic nerve fibers which project into the memory and learning centers, i.e., the cerebral cortex and hippocampus, from the cerebral basal ganglia and dysfunctions in said controlled areas caused by this change. In fact, a few case reports showed that the symptoms were slightly improved by administering an acetylcholine biosynthesis precursor or a cholinesterase inhibitor as an activator to SDAT patients in order to activate the cholinergic system in the brain. However, in general, the observed effects were not so significant as expected.

Since discovery of NGF by R. Levi-Monterlcini, S. Cohen and others, considerable research on NGF has been carried out. To date, it has been proved by physiological experiments that NGF is an essential factor for differentiation and growth of sensory and sympathetic nerve cells in the peripheral nervous system, particularly in the embryonal period, and further for the survival of the sympathetic nerve cells and maintenance of their functions in the maturation period.

However, because NGF is a physiologically active substance which exists only in an extremely small quantity, accurate knowledge regarding distribution and movement of NGF in tissues, which directly demonstrates the action of NGF in the body, has not been attained in spite of intensive research for a long period of time. Only recently, a highly sensitive enzyme-linked immunosorbent assay (hereinafter referred to as ELISA) for an active subunit of NGF (beta-NGF, hereinafter simply designated as NGF) was developed and improved with sufficient sensitivity and specificity to study the matters described above (S. Furukawa et al.: J. Neurochem., 40, 734–744, 1983 and S. Korshing and H. Thoenen: Proc. Natl. Acad. Sci., USA, 80, 3513–3516, 1983).

Furthermore, the NGF gene was cloned and its structure was analyzed, which makes it possible to establish a method for the quantitative measurement of its messenger RNA (hereinafter abbreviated as mRNA) by using the complementary DNA (hereinafter abbreviated as cDNA) of beta-NGF (D. L. Shelton and L. F. Reichardt: Proc. Natl. Acad. Sci., USA, 81, 7951–7955, 1984 and R. Heumann et al.: EMBO J., 3, 3183–3189, 1984).

Then, using the techniques described above, it was proved that there is a positive correlation between the degree of control by the sympathetic nerve in the peripheral nervous system and expression of the NGF gene in the tissues being controlled.

More surprisingly, NGF is detected also in the central nervous system, particularly in the hippocampus, the neocortex, the septal area of the olfactory bulb and basal forebrain, the Broca's diagonal band and the large cell basal ganglia, and moreover mRNA concentrations are high in the hippocampus and the neocortex and are as low in the septal area of the basal forebrain as in other brain areas where NGF is not detected (S. Korshing et al.: EMBO J., 4, 1389–1393, 1985). Later these observations were re-examined one after another by other research groups (D. L. Shelton and L. F. Reichardt: Proc. Natl. Acad. Sci., USA 83, 2714–2718, 1986 and S. Whittemore et al.: Proc. Natl. Acad. Sci., USA, 83, 817–821, 1986).

These findings demonstrate that the NGF gene is expressed not only in the peripheral nervous system but also in the central nervous system and moreover that NGF is produced and secreted in the areas controlled by cholinergic nerve fibers which project into the neocortex and hippocampus, i.e., the memory and learning center, from the nucleus of origin of the cerebral ganglia, captured at the nerve endings and then brought to the cellular body of the nucleus of origin by reverse axon transport. It was proved by a series of physiological experiments that NGF is an essential factor for the survival of these cholinergic nerve cells and maintenance of their functions; it was thus proved from these observations that NGF specifically functions also in the central nervous system as one of the "nerve nutrition factors".

Later, these findings were re-examined by various research groups and also verified from research on NGF receptors and NGF distribution in the brain.

During the course of the research on the function of NGF in the central nerve system as a nerve nutrition factor, the present inventors concluded that although a direct cause of the disturbance in memory and learning, which is an early symptom of SDAT, may be progressive changes of the cholinergic nerve fibers and dysfunction caused by these changes in the areas being controlled, the disease may be caused more fundamentally by disturbance in production and secretion of NGF in these areas being controlled by responsible nerves.

In other words, the present inventors believe that marked improvement cannot be attained by conventional nosotrophic therapy for SDAT, for example by providing acetylcholine or by increasing availability of acetylcholine, but it may be far more effective as a therapy to secure the production and excretion of NGF in the cerebral cortex and hippocampus so as to stop a functionally vicious cycle established within the controlling nerves, if possible.

However, great pharmaceutical and pharmacological difficulties still exist in substitution therapy using NGF itself which is a protein having a molecular weight of more than 10,000 although a way of possible mass production of human type beta-NGF by cloning of the gene has opened. In particular, as to the application to the central nerve system, the prospect of development is still far from certain.

From the point of view mentioned above, for a substantial and effective NGF substitution therapy, it is of great importance to search for a low molecular weight molecule which can induce production and excretion of NGF in specified tissues. The present inventors have already reported on catechol derivatives which have this action (for example, Fukazawa: Japanese Patent Laid-open No. 53767/1990 and No. 152950/1990). Furthermore, there are reports by Furukawa et al. (Y. Furukawa et al.: J. Biol. Chem., 261, 6039, (1986) and FEBS Letters, 208, 258, (1986)).

As mentioned above, it is expected that compounds and modified compounds thereof, being modified based on pharmacological and pharmaceutical considerations, have a capability to promote production and secretion of NGF which functions as the "nerve nutrition factor" and acts on specific nerves in the tissues being controlled, and thus possibly increase the amount of available NGF to degenerated sites of the nerves by means of ordinary administration of said compounds, thereby recovering the functions of said specific nerves. In particular, use of these compounds for the therapy of SDAT, a disease in the central nervous system for which fundamental therapy has not yet been established, is ideal. If treated in the early stage of the disease and administered at the peripheral system, these compounds enhance capability of NGF production and secretion in the cerebral cortex and the hippocampus area in the central nervous system, prevent the progress of characteristic changes in the nerves being controlled by NGF, i.e., the cholinergic nerve system, and promote repair of damaged nerve cells or re-control by remaining nerve cells, thereby providing a revolutionary therapy based on the new action concept attributed to flexibility of brain functions.

However, later, research showed that none of the catechol derivatives so far reported were satisfactorily absorbable or retainable when orally administered. The present inventors continued their study in order to solve this problem and consequently found that the compounds of the present invention are increasingly absorbable when orally administered and their retention in the blood is highly improved as compared to the compounds described in Japanese Patent Laid-open No. 152950/1990 and No. 99046/1991 which were applied previously by the present inventors. Furthermore, it was found that the amount of NGF increased in various parts of brain when the compounds of the present invention were orally administered to rats, with which the present invention was deemed to be completed.

DISCLOSURE OF THE INVENTION

Accordingly, the present invention comprises first pharmaceutical agents containing amide derivatives of dihydroxycaffeic acid represented by the general formula (I) and their salts as effective constituents for the prevention of the progression of degenerative diseases in the central nervous system and the therapeutic treatment thereof,

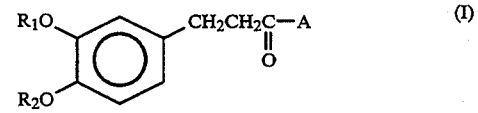

(in which $R_1$ and $R_2$ can be identical or different and are a hydrogen atom, an alkyl group having 1–4 C atoms, an aryl, propargyl, benzyl or pyridylmethyl group, or $R_1$ and $R_2$ are bound together to form a —CH2CH2— group or —CR$_3$R$_4$— group wherein $R_3$ and $R_4$ are each independently a hydrogen atom, an alkyl group having 1–4 C atoms or a phenyl group; A is a cyclohexylamino group, —NR$_5$R$_6$,

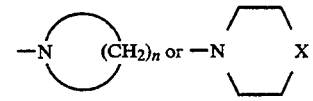

wherein $R_5$ is a hydrogen atom or an alkyl group having 1–6 C atoms; $R_6$ is an alkyl group having 1–6 C atoms; n is an integer from 2 to 7 exclusive; X is an oxygen atom or a =NR$_7$ group wherein $R_7$ is a hydrogen atom or an alkyl group having 1–4 C atoms; the case where $R_1$ and $R_2$ in the formula are both hydrogen atoms is excluded.)

In the general formula (I), $R_1$ and $R_2$ can be identical or different as defined above but are preferably identical. A is preferably

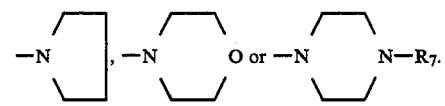

In the general formula (I), the alkyl groups having 1–4 C atoms of $R_1$, $R_2$, $R_3$, $R_4$, $R_7$ and $R_8$ include methyl, ethyl, propyl, isopropyl and butyl groups. The alkyl groups having 1–6 C atoms of $R_5$ and $R_6$ include methyl, ethyl, propyl, butyl, pentyl and hexyl group. Examples of the

group of A include aziridyl, azetidyl, pyrrolidyl and piperidyl groups. Examples of the

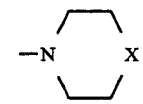

group of A include morpholino, piperazinyl and 4-methyl-1-piperazinyl groups.

Furthermore, among the compounds represented by the general formula (I), the following compounds are novel compounds and thus the second aspect of the invention is the invention of these novel compounds.

Namely, the first group of compounds are amide derivatives of dihydrocaffeic acid of the general formula (I) and their salts, in which A is as defined above and $R_1$ and $R_2$ are an aryl, propargyl, benzyl or pyridylmethyl group or otherwise $R_1$ and $R_2$ are bound together to form a —$CH_2CH_2$— group or a —$CR_3R_4$— group (in which $R_3$ and $R_4$ are each independently a hydrogen atom or an alkyl group having 1–4 C atoms or a phenyl group; the case where $R_3$ and $R_4$ are both hydrogen atoms is excluded.)

The second group of the compounds are amide derivatives of dihydrocaffeic acid represented by the following general formula (II) and their salts,

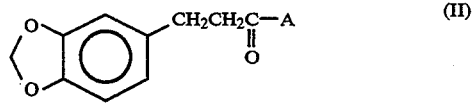

(in which A is a cyclohexylamino group, —$NR_6R_6$,

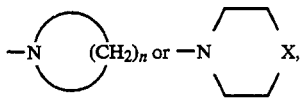

wherein $R_6$ is an alkyl group having 1–6 C atoms; n is an integer from 2 to 7 except 5; and X is an oxygen atom or a =$NR_7$ group wherein $R_7$ is an alkyl group having 1–4 C atoms).

Furthermore, the third group of the compounds are amide derivatives of dihydrocaffeic acid of the general formula ( I ) and their salts, in which $R_1$ and $R_2$ can be identical or different and are each a hydrogen atom or an alkyl group having 1–4 C atoms but not together hydrogen atoms; and A is a cyclohexylamino group,

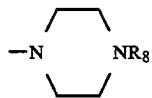

(wherein $R_5$ is a hydrogen atom or an alkyl group having 1–6 C atoms; $R_6$ is an alkyl group having 1–6 C atoms and $R_8$ is an alkyl group having 1–4 C atoms).

The compounds of the present invention (represented by the general formula (I)) can be the pharmacologically acceptable salts. Examples of these salts include salts of alkali metals or alkaline earth metals such as sodium salts, potassium salts or calcium salts, salts of basic amino acids such as lysine or appropriate organic bases in the case where the compounds have acidic groups. On the other hand, if the compounds have basic groups, examples of these salts include salts of halogenized hydroacid, such as hydrofluoric acid, hydrochloric acid, hydrobromic acid or hydroiodic acid, salts of inorganic acids such as nitric acid, perchloric acid, sulfuric acid or phosphoric acid, salts of lower alkylsulfonic acids, such as methanesulfonic acid, trifluoromethanesulfonic acid or ethanesulfonic acid, salts of arylsulfonic acids, such as benzensulfonic or p-toluenesulfonic acid, salts of organic acids, such as fumaric acid, succinic acid, citric acid, tartaric acid, oxalic acid, maleic acid or ascorbic acid, and salts of acidic amino acids such as glutamic or aspattic acid.

Processes of manufacturing the compounds of the present invention will be described as follows:

In the first method, a dihydrocaffeic acid ethyl ester which is readily available and a corresponding amine are thermally condensed to obtain a compound of amide derivative of dihydrocaffeic acid of the general formula (I) in which $R_1$ and $R_2$ are both hydrogen atoms. This method is disclosed in Japanese Patent Laid-open No. 53767/1990 and No. 152950/1990. A target compound is obtained by reacting this compound with a compound having the general formula $R_1$—X, X—$C_2C_2$—X or X—$CR_3R_4$—X (in which $R_1$, $R_3$ and $R_4$ are as defined above and X is a chlorine, bromine or iodine atom) in the presence of a base normally in a molar ratio of the former to the latter of 1:1 to 1:10. The base being used here is an inorganic base such as sodium hydroxide, potassium hydroxide, potassium carbonate or sodium hydrogencarbonate or an organic base such as pyridine, triethylamine, dimethylamine, sodium methoxide or potassium tert-butoxide. Further, metal copper or cupric oxide can be added to the reaction mixture.

There is no limit as to the solvent being used. For example, water, methanol, acetone, benzene, toluene, tetrahydrofuram or dimethylfomamide is used alone or in combination. In this case, reaction temperature ranges preferably from 0° C. to the boiling point of the solvent used.

In the second method, a dihydrocaffeic acid ethyl ester and a compound of the above-mentioned general formula $R_1$—X, X—$CH_2CH_2$—X or X—$CR_3R_4$—X (in which $R_1$, $R_3$ and $R_4$ are the same as defined above) are first reacted also in the presence of a base normally in a molar ratio of the former to the latter of 1:1 to 1:10. In this case, the kind of base and reaction conditions are the same as previously described. Subsequently, the resultant compound (an ester) is thermally condensed with a corresponding amine or a carboxylic acid compound obtained by hydrolysis is reacted with thionyl chloride, phosphorus pentachloride or the like to make an acid chloride and then condensed with a corresponding amine, or otherwise the carboxylic acid is condensed with a corresponding amine using various condensing agents. The term "thermally" herein used means that heating is carried out at a temperature ranging from room temperature to, in a certain cases, 200° C. In this case, the reaction proceeds mostly in the absence of solvent; in certain cases, an excessive amount of the corresponding amine or an inactive solvent such as toluene or xylene can be used. Further, the various condensing agents mean those which are normally used in the field of peptide chemistry, such as DCC (dicyclohexylcarbodimide) or CDI (carbonyldimidazole).

The methods described above are shown with chemical formulae as follows: The first method is:

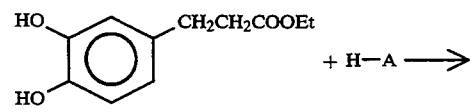

-continued

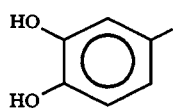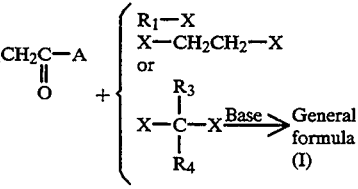

The second method is:

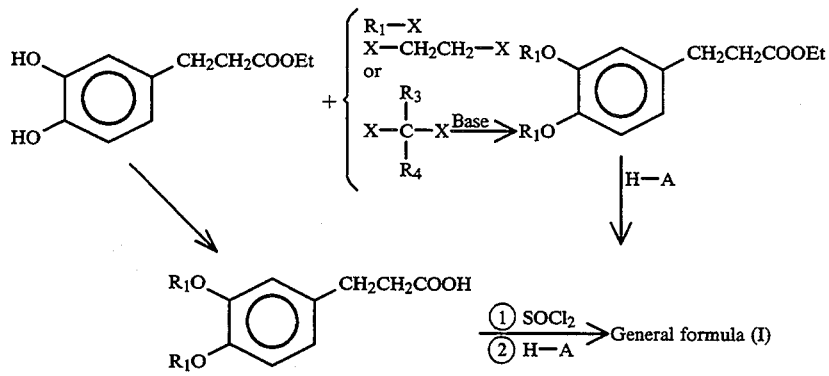

[in the formulae, $R_1$, $R_3$, $R_4$ and X are the same as defined above. H-A represents an amine corresponding to A in the formula (I).]

Furthermore, among the compounds of the general formula (I) according to the present invention, a group of compounds in which $R_1$ and $R_2$ are bound together to form $-CR_3R_4-$ (in which $R_3$ and $R_4$ are as defined above) are obtained by reacting compounds in which $R_1$ and $R_2$ are together hydrogen atoms in the dihydroxycaffeic acid amide derivative of the general formula (I) and a compound represented by the general formula $R_3R_4CO$ or $R_3R_4(OCH_3)_2$ (in which $R_3$ and $R_4$ are as defined above) normally in a molar ratio of the former to the latter of 1:1 to 1:5. There is no limit as to solvent being herein used; benzene, toluene, xylene, tetrahydrofuran or the like can be preferably used alone or in combination. In certain cases, an acid such as sulfuric acid or p-toluenesulfonic acid is added. The reaction temperature ranges from room temperature to the boiling point of the solvent being used, preferably the azeotropic point of water and the solvent being used in order to remove generated water.

The following compounds are obtained in analogous reactions and treatments:

N-butyl-3-(2-phenyl-1,3-benzodioxol-6-yl)propionamide,
N-butyl-3-(3,4-dipyridylmethyloxphenyl)propionamide,
N-methyl-N-butyl-3-(1,4-benzodioxane-6-yl)propionamide,
N-methyl-N-butyl-3-(3,4-dimethoxyphenyl)propionamide,
N-methyl-N-butyl-3-(3,4-dipropargyloxyphenyl)propionamide,
N-methyl-N-butyl-3-(3,4-dipropyloxyphenyl)propionamide,
N-methyl-N-butyl-3-(2-methyl-1,3-benzodioxol-6-yl)propionamide,
N-methyl-N-butyl-3-(2,2-dimethyl-1,3-benzodioxol-6-yl)propionamide,
N-methyl-N-butyl-3-(2-phenyl-1,3-benzodioxol-6-yl)propionamide,
N-methyl-N-butyl-3-(3,4-dipyridylmethyloxyphenyl)-propionamide,
N-cyclohexyl-3-(3,4-dimethoxyphenyl)propionamide,
N-cyclohexyl-3-(3,4-dipropargyloxyphenyl)propionamide,
N-cyclohexyl-3-(2-phenyl-1,3-benzodioxol-6-yl)propionamide,
N-cyclohexyl-3-(2,2-dimethyl-1,3-benzodioxol-6-yl)propionamide,
N-[3-(1,4-benzodioxane-6-yl)propionyl]pyrrolidine,
N-[3-(3,4-dibenzyloxyphenyl)propionyl]piperazine,
N-[3-(3,4-dipropargyloxyphehyl)propionyl]morpholine,
N-[3-(3,4-diaryloxyphenyl)propionyl]pyrrolidine,
N-[3-(2-methyl-1,3-benzodioxol-6-yl)propionyl]morpholine,
N-[3-(2,2-dimethyl-1,3-benzodioxol-6-yl)propionyl]morpholine,
N-[3-(3,4-dipyridylmethyloxyphenyl)propionyl]morpholine, N,N-dimethyl-3-(3,4-methylenedioxyphenyl)propionamide,
N-methyl-N-ethyl-3-(3,4-methylenedioxyphenyl)propionamide,
N,N-diethyl-3-(3,4-methylenedioxyphenyl)propionamide,
N,N-dipropyl-3-(3,4-methylenedioxyphenyl)propionamide,
N,N-dibutyl-3-(3,4-methylenedioxyphenyl)propionamide,
N,N-dipentyl-3-(3,4-methylenedioxyphenyl)propionamide,
N-[3-(3,4-methylenedioxyphenyl)propionyl]piperidine,
N-butyl-3-(3,4-methylenedioxyphenyl)propionamide,
N-pentyl-3-(3,4-methylenedioxyphenyl)propionamide,
N-hexyl-3-(3,4-methylenedioxyphenyl)propionamide,
N-[3-(3-methoxy-4-hydroxyphenyl)propionyl]piperidine,
N-butyl-3-(3-methoxy-4-hydroxyphenyl)propionamide,
N-cyclohexyl-3-(3-methoxy-4-hydroxyphenyl)propionamide,
N-methyl-N-butyl-3-(3-methoxy-4-hydroxyphenyl)propionamide.

Effectiveness of the compounds of the present invention as pharmaceutical agents for the prevention of the progressions of degenerative diseases in the central nervous system and the therapeutic treatment thereof was confirmed by the following experiments: Namely, it was previously reported that the compounds of the general formula (I) in which $R_1$ is a hydrogen atom as represented below

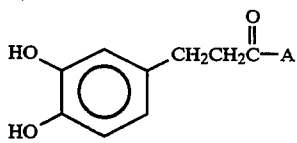

(in which A is the same substituent group as defined above) exerted an extremely strong action to promote NGF production and secretion in a system in which L-M cells of a mouse fibroblast cell line and astroglia cells, which are known as important cells for NGF production and excretion in tissues in the central nervous system, were used (Japanese Patent Laid-open No. 53767/1990 and No. 152950/1990). The compounds of the present invention represented by the general formula (I) are those in which the hydrogen atoms of the compound described above are protected by various substitute groups described above and they are thus so-called pro-drug compounds. Namely, the compounds of the formula represented above were modified so as to improve their enteral absorbability, durability in the blood and capability to reach the brain tissues, which increases medicinal effectiveness. In fact, after the compounds of the present invention were orally administered to rats, measurements in the blood showed that the compounds were maintained in high concentrations for a long period of time, thereby the effectiveness being confirmed. Furthermore, when the compounds of the present invention were orally administered to rats at a dose of 1-5 mg/kg body weight, marked increase in NGF concentrations in the brain tissues was observed; the high NGF concentrations were detected particularly in areas of the flotal lobe cortex and hippocampus. Furthermore, marked anti-dementia effect was detected in various animal model experiments for anti-dementia study using rats. Thus it was confirmed that the compounds of the present invention can make effective agents for the prevention of the progression of generative diseases in the central nervous system, especially SDAT, and the therapeutic treatment thereof.

Furthermore, when the compounds of the present invention are used as pharmaceutical agents for the prevention of the progression of degenerative diseases in the central nervous system and the therapeutic treatment thereof, the dosage and form of agents naturally vary depending on physical properties of the compounds, the symptoms of a patient to be treated or the like; however, a daily dose of 50-500 mg for adult in one or several dosages in a form of tablet, granule, powder, suspension, capsule or the like can be used for oral administration and a daily dose of 1-100 mg for adult in one or several dosages in a form of injectable preparation, suppository, transfusion or the like can be used for parenteral administration.

For example, when the compounds are used in tablet form, crystalline cellulose, light dehydrated silica or the like is used as an absorbent and corn starch, lactose, calcium phosphate, magnesium stearate or the like can be used as an excipient.

Furthermore, when the compounds are used in an injectable preparation, it can be in the form of aqueous solution, suspension in water using cotton seed oil, corn oil, peanut oil, olive oil or the like, and furthermore, emulsion, for example, with surface active agents such as HCO-60 or the like.

Furthermore, there is no limit as to the amount of effective ingredients in the agents; in general 0.1-99% by weight, preferably 1.0-50% by weight is used.

BEST MODE OF CARRYING OUT THE INVENTION

The present invention will be illustrated in more detail by the following examples. However, it is to be understood that the invention is not intended to be limited to these examples.

| Example of Pharmaceutical preparation - 1 (Capsules) | |
|---|---|
| N-[3-(1,3-benzodioxol-5-yl)propionyl]pyrrolidine (Compound in Example 12) | 50 mg |
| Lactose | 150 mg |
| Corn starch | 85 mg |
| Calcium phosphate | 5 mg |

The ingredients described above were mixed and then made into capsules using a capsule filling machine.

EXAMPLE 1

N-butyl-3-(3,4-dimethoxyphenyl)propionamide 1.5 g of N-butyl-3-(3,4-dihydroxyphenyl)propionamide was dissolved in 10 ml of N,N-dimethylformamide and 2.3 g of potassium carbonate anhydride was added to the solution. 1.5 ml of methyl iodide was then added to the solution and the resulting solution was stirred at room temperature for 4 hours and allowed to stand overnight. The solution was then poured over iced water and extracted with ethyl acetate; the organic phase was isolated, washed with water, dried with sodium sulfate, the solvent being removed by evaporation under reduced pressure. The residue was purified by chromatography on a silica gel column with a mixed solvent (chloroform:methanol=100:1) and 0.87 g of N-butyl-3-(3,4-dimethoxyphenyl)propionamide was obtained as a crystalline powder.

EXAMPLES 2, 3, 4, 5, 6 AND 7

Compounds of Examples 2, 3, 4, 5, 6 and 7 shown in Table 1 were obtained using the same kind of reactions and procedures as described in Example 1.

EXAMPLE 8

N-butyl-3-(1,4-benzodioxane-6-yl)propionamide 1.5 g of N-butyl-3-(3,4- dihydroxyphenyl)propionamide was dissolved in 10 ml of N,N-dimethylformamide and 2.3 g of potassium carbonate anhydride was added to the solution. Then 2.3 g of 1,2-dibromoethane and 100 mg of cupric oxide were added to the solution and the resulting solution was stirred at 130°-140° C. for 4 hours. After cooling, the solution was poured over iced water and extracted with ethyl acetate; the organic layer was isolated, washed with water, dried with sodium sulfate anhydride and the solvent was removed by evaporation under reduced pressure. The residue was purified by chromatography on a silica gel column with a mixed solvent (chloroform:methanol=100:1) and thus 0.62 g of oily N-butyl-3-(1,4-benzodioxane-6-yl)propionamide was obtained.

EXAMPLE 9

A compound of Example 9 shown in Table 1 was obtained using the same kind of reactions and procedure as described in Example 8.

EXAMPLE 10

N-butyl-3-(2,2-dimethyl-1,3-benzodioxol-5-yl)propionamide 1.5 g of N-butyl-3-(3,4- dihydroxyphenyl)propionamide was dissolved in a mixed solvent consisting of 30 ml of benzene and 10 ml of tetrahydrofuran and 4 ml of acetonedimethylacetal was added to the solution. Then a small amount of p-toluenesulfonic acid was added to the solution and the solution was stirred for 11 hours under reflux. With a further addition of 2 ml of acetonedimethyl acetal, stirring was continued under reflux for 6 hours. After cooling, the solution was poured over ice water containing sodium hydrogen carbonate and was mixed thoroughly. The solution was extracted with ethyl acetate, washed with water and then dried with sodium sulfate anhydride. After removing the solvent by evaporation under reduced pressure, the resulting residue was purified by chromatography on silica gel column using a mixed solvent (chloroform::methanol=100:1) and thus 0.84 g of oily N-butyl-3-(2,2-dimethyl-1,3-benzodioxol-5-yl)propionamide was obtained.

EXAMPLE 11

A compound of Example 11 shown in Table 1 was obtained in the same kind of reactions and procedure as described in Example 10.

EXAMPLE 12

N-[3-(1,3-benzodioxol-5-yl)propionyl]pyrrolidine 0.92 g of N-[3-(3,4-dihydroxyphenyl)-propionylpyrrolidine was dissolved in 10 ml of N,N-dimethylformamide and then 1.2 g of dibromomethane and 1.2 g of potassium carbonate anhydride and 100 mg of cupric oxide were added to the solution and the resulting solution was stirred at 130°–140° C. for 4 hours. After cooling, the solution was poured over iced water, extracted with ethyl acetate, washed with water and then dried with sodium sulfate anhydride. The solvent was removed by evaporation under reduced pressure and the residue was purified by chromatography on a silica gel column with a mixed solvent (chloroform:methanol=100:1) and thus 0.59 g of oily N-[3-(1.3-benzodioxol-5-yl)propionyl]pyrrolidine was obtained.

EXAMPLES 13, 14, 15, 16, 17, 18 AND 19

Compounds of Examples 13, 14, 15, 16, 17, 18 and 19 shown in Table 1 were obtained by the same kind of reactions and procedure as described in Example 12.

EXAMPLE 20

N-[3-(3,4-dipyridylmethyloxyphenyl)propionyl]piperidine 2.0 g of N-[3-(3,4-dihydroxyphenyl)propionyl]piperidine was dissolved in 50 ml of N,N-dimethylfomamide and then 1.8 g of potassium tert-butoxide was added to the solution under icy cooling. The solution was brought into room temperature and was stirred for 30 minutes and then 2.5 g of 3-chloromethylpyridine was added to the solution. After stirring for 1 hour, the solution was concentrated. The concentrate was dissolved in ethyl acetate, washed with water and dried with sodium sulfate anhydride. The solvent was removed by evaporation under reduced pressure and the residue was purified by chromatography on a silica gel column with a mixed solvent (chloroform:methanol=50:1) and thus 1.07 g of oily N-[3-(3,4-dipyridylmethyloxyphenyl)propionyl]piperidine was obtained.

TABLE 1

Compounds of the persent invention

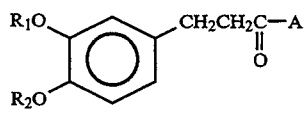

| Example No. | R1 and R2 Structure | A | Melting point (°C.) | IR$\nu_{cm^{-1}}^{max}$ | NMR$\delta$ppm (CDCl3) |
|---|---|---|---|---|---|
| 1 | CH3— | H<br>CH3(CH2)3N— | 58–60 | 2934, 1644, 1518, 1261, 1155, 1139, 1028, 850 (KBr) | 0.89(3H, t), 1.23–1.31(2H, m), 1.37–1.43(2H, m), 2.43 (2H, t), 2.90(2H, t), 3.18–3.23(2H, m), 3.85(3H, s), 3.86 (3H, s), 5.35–5.45(1H, broad), 6.71–6.77(3H, m) |
| 2 | HC≡CCH2— | H<br>CH3(CH2)3N— | 90–92 | 2930, 1635, 1524, 1453, 1263, 1219, 1140, 1019 (KBr) | 0.89(3H, t), 1.22–1.31(2H, m), 1.37–1.44(2H, m), 2.41–2.50(4H, m), 2.89–2.93(2H, m), 3.18–3.23(2H, m), 4.72–4.74(4H, m), 5.25–5.4(1H, broad), 6.78–6.98(3H, m) |
| 3 | C6H5-CH2— | H<br>CH3(CH2)3N— | 108–110 | 3314, 1638, 1545, 1517, 1258, 1224, 1134, 1018 (KBr) | 0.88(3H, t), 1.19–1.28(2H, m), 1.32–1.40(2H, m), 2.35 (2H, t), 2.84(2H, t), 3.13–3.18(2H, m), 5.11(2H, s), 5.13 (2H, s), 5.05–5.25(1H, broad), 6.67–6.85(3H, m), 7.26–7.45(10H, m) |
| 4 | H2C=CHCH2— | H<br>CH3(CH2)3N— | 61–63 | 3083, 1640, 1549, 1423, 1267, 1137, 1019, 917 (KBr) | 0.89(3H, t), 1.22–1.31(2H, m), 1.36–1.44(2H, m), 2.41 (2H, t), 2.88(2H, t), 3.17–3.22(2H, m), 4.56–4.58(4H, m), 5.2–5.5(5H, m), 6.0–6.15(2H, m), 6.69–6.81(3H, m) |

TABLE 1-continued

Compounds of the persent invention $$R_1O-C_6H_3(OR_2)-CH_2CH_2C(=O)-A$$

| Example No. | Structure R₁ and R₂ | Structure A | Melting point (°C.) | IR $\nu_{cm^{-1}}^{max}$ | NMR δppm (CDCl₃) |
|---|---|---|---|---|---|
| 5 | Ph—CH₂— | piperidin-1-yl | Oily substance | 2936, 2857, 1639, 1512, 1454, 1263, 1137, 1024, 748, 697 (neat) | 1.4–1.6(6H, m), 2.5–2.6(2H, m), 2.8–2.9(2H, m), 3.27 (2H, t), 3.53(2H, t), 5.12(2H, s), 5.14(2H, s), 6.7–6.9 (3H, m), 7.2–7.5(10H, m) |
| 6 | HC≡C—CH₂— | piperidin-1-yl | Oily substance | 3287, 2938, 2858, 1632, 1511, 1445, 1254, 1137, 1024 (neat) | 1.4–1.7(6H, m), 2.5–2.7(4H, m), 2.9–3.0(2H, m), 3.34 (2H, t), 3.55(2H, t), 4.7–4.8(4H, m), 6.8–7.0(3H, m) |
| 7 | H₂C=CH—CH₂— | piperidin-1-yl | Oily substance | 2936, 2857, 1640, 1512, 1256, 1218, 1138, 1020, 926 (neat) | 1.4–1.7(6H, m), 2.5–2.6(2H, m), 2.8–2.9(2H, m), 3.32 (2H, t), 3.55(2H, t), 4.5–4.6(4H, m), 5.2–5.5(4H, m), 6.0–6.2(2H, m), 6.7–6.8(3H, m) |
| 8 | —CH₂—CH₂— (R₁=R₂, methylenedioxy) | CH₃(CH₂)₃NH— | Oily substance | 2873, 1644, 1508, 1433, 1287, 1206, 1126, 1070 (neat) | 0.90(3H, t), 1.24–1.30(2H, m), 1.37–1.43(2H, m), 2.40 (2H, t), 2.84(2H, t), 3.18–3.23(2H, m), 4.22(4H, s), 5.35–5.45(1H, broad), 6.64–6.77(3H, m) |
| 9 | —CH₂—CH₂— | piperidin-1-yl | Oily substance | 2935, 2857, 1640, 1508, 1442, 1285, 1258, 1069, 887, 816 (neat) | 1.4–1.7(6H, m), 2.5–2.6(2H, m), 2.8–2.9(2H, m), 3.34 (2H, t), 3.55(2H, t), 4.23(4H, s), 6.6–6.8(3H, m) |
| 10 | (H₃C)₂C< | CH₃(CH₂)₃NH— | Oily substance | 2934, 1644, 1557, 1498, 1254, 1156, 981, 840 (neat) | 0.89(3H, t), 1.2–1.35(2H, m), 1.35–1.45(2H, m), 1.65 (6H, s), 2.35–2.45(2H, m), 2.8–2.9(2H, m), 3.18–3.23 (2H, m), 5.4–5.5(1H, broad), 6.57–6.63(3H, m) |
| 11 | (H₃C)₂C< | piperidin-1-yl | Oily substance | 2936, 2856, 1644, 1497, 1444, 1376, 981, 838 (neat) | 1.4–1.7(6H, m), 1.65(6H, s), 2.5–2.6(2H, m), 2.8–2.9 (2H, m), 3.34(2H, t), 3.55(2H, t), 6.6–6.7(3H, m) |
| 12 | >CH₂ (cyclic) | pyrrolidin-1-yl | Oily substance | 2876, 1637, 1443, 1246, 1190, 1039, 928, 810 (neat) | 1.80–1.90(4H, m), 2.49–2.53(2H, m), 2.88–2.96(2H, m), 3.31(2H, t), 3.46(2H, t), 5.91(2H, s), 6.66–6.73(3H, m) |
| 13 | >CH₂ | morpholin-4-yl | Oily substance | 2859, 1644, 1490, 1443, 1246, 1115, 1038, 928 (neat) | 2.56(2H, t), 2.89(2H, t), 3.3–3.4(2H, m), 3.5–3.7(6H, m), 5.92(2H, s), 6.64–6.73(3H, m) |
| 14 | >CH₂ | 4-methylpiperazin-1-yl | Oily substance | 2795, 1644, 1444, 1247, 1039, 1003, 929, 811 (neat) | 2.28(3H, s), 2.2–2.4(4H, m), 2.5–2.6(2H, m), 2.85–2.95 (2H, m), 3.35–3.45(2H, m), 3.6–3.7(2H, m), 5.91(2H, s), 6.6–6.8(3H, m) |
| 15 | >CH₂ | CH₃(CH₂)₃N(CH₃)— | Oily substance | 2932, 1644, 1490, 1443, 1246, 1040, 929, 810 (neat) | 0.92(3H, t), 1.25–1.32(2H, m), 1.44–1.52(2H, m), 2.52–2.58 (2H, m), 2.85–2.95(5H, m), 3.20(1H, m), 3.36(1H, m), 5.91(2H, s), 6.65–6.73(3H, m) |
| 16 | Ph—CH< | morpholin-4-yl | Oily substance | 2856, 1644, 1496, 1444, 1245, 1115, 1021, 850 (neat) | 2.55–2.65(2H, m), 2.9–3.0(2H, m), 3.35–3.5(2H, m), 3.5–3.8(6H, m), 6.65–6.8(3H, m), 6.93(1H, s), 7.4–7.65(5H, m) |

TABLE 1-continued

Compounds of the persent invention $$R_1O-C_6H_3(OR_2)-CH_2CH_2C(=O)-A$$

| Example No. | Structure R₁ and R₂ | A | Melting point (°C.) | IR$\nu_{cm-1}^{max}$ | NMR δppm (CDCl₃) |
|---|---|---|---|---|---|
| 17 | CH₂=CH-CH₂- (allyl, both) | cyclohexyl-NH- | 140-142 | 2931, 1639, 1547, 1445, 1246, 1187, 1106, 1042 (KBr) | 1.0-1.9(10H, m), 2.37(2H, t), 2.86(2H, t), 3.7-3.8(1H, m), 5.15-5.25(1H, broad), 5.91(2H, s), 6.62-6.72(3H, m) |
| 18 | C₆H₅-CH< (benzyl-type, both) | piperidino (N-) | Oily substance | 2937, 2857, 1638, 1495, 1443, 1247, 1020, 760, 698 (neat) | 1.4-1.7(6H, m), 2.5-2.6(2H, m), 2.8-2.9(2H, m), 3.2-3.45(2H, broad), 3.45-3.7(2H, broad), 6.6-6.8(3H, m), 6.92(1H, s), 7.3-7.6(5H, m) |
| 19 | CH₃CH< (both) | piperidino (N-) | Oily substance | 2936, 2857, 1641, 1496, 1444, 1246, 1097, 867, 807, 752 (neat) | 1.4-1.7(6H, m), 1.66(3H, d), 2.5-2.6(2H, m), 2.8-2.9(2H, m), 3.34(2H, t), 3.55(2H, t), 6.21(1H, q), 6.6-6.7(3H, m) |
| 20 | pyridyl-CH₂- (both) | piperidino (N-) | Oily substance | 2937, 2857, 1634, 1512, 1257, 1137, 1022, 854, 795, 712 (neat) | 1.4-1.7(6H, m), 2.5-2.6(2H, m), 2.85-2.95(2H, m), 3.32 (2H, t), 3.54(2H, t), 5.10(2H, s), 5.12(2H, s), 6.75-6.9(3H, m), 7.25-7.35(2H, m), 7.7-7.8(2H, m), 8.5-8.6(2H, m), 8.6-8.7(2H, m) |

EXPERIMENTAL EXAMPLE 1

Action on NGF Production in Rat Brain

Each compound to be tested was orally given to a 6 week old rat three times, i.e., in the morning, in the evening and in the following morning. Four hours after the final administration, the rat was decapitated under anesthesia and bled and then the whole brain was extracted immediately. The extracted brain was divided into individual tissues, i.e., the frontal love cortex, septal area, hippocampus, striate body and cerebral cortex in an ice-cold petri dish; each tissue was then rapidly lyophilized in an Eppendorf tube by liquid nitrogen and kept frozen at −80° C. until use. For use, an appropriate amount of each tissue (about 10–50 mg) was measured out and an ice-cold homogenizing buffer (20 mM Tris-HCl, pH 7.6, 0.5M NaCl, 10 mM EDTA, 2% BSA, 0.5% Tween 20, 20 U/ml aprotinin, 0.1 mM PMSF) was added to the tissue, 2–3% (w/v) in the case of septal area and 5% (w/v) in the case of other tissues, and the mixture was homogenized 40 times using a glass homogenizer. Subsequently, the homogenized fraction was centrifuged using an ultra-centrifuge at 4° C. for 10 minutes at 100,000×g and the resulting supernatant was kept frozen at −20° C. as a sample for ELISA measurement until use. The extract was further centrifuged at a low speed (10,000 rpm for 10 minutes) after melting and then subjected to the measurement NGF concentration was measured by the method of Furukawa et al. (S. Furukawa et al., J. Neurochem., 40, 734–744, 1983). A calibration curve was made using a beta-NGF standard solution. The results are given in Table 2. All the compounds tested showed similar marked stimulative action on NGF production.

TABLE 2

Action on NGF production $$R_1O-C_6H_3(OR_2)-CH_2CH_2C(=O)-A$$

| | Structure | | | NGF increase (Control = 100) | | |
|---|---|---|---|---|---|---|
| Example No. | R₁ and R₂ | A | Dose (mg/kg) | Striate body | Frontal lobe | Hippocampus |
| 2 | HC≡C-CH₂- | H, CH₃(CH₂)₃N- | 1 | 110 | 132 | 140 |
| 3 | C₆H₅-CH₂- | H, CH₃(CH₂)₃N- | 3 | 103 | 124 | 125 |

TABLE 2-continued

Action on NGF production $$R_1O-\text{(phenyl)}-CH_2CH_2\underset{O}{\overset{\|}{C}}-A$$

with $R_2O$ on the ring.

| Example No. | Structure R₁ and R₂ | Structure A | Dose (mg/kg) | NGF increase (Control = 100) Striate body | Frontal lobe | Hippocampus |
|---|---|---|---|---|---|---|
| 4 | H₂C=CHCH₂— | H, CH₃(CH₂)₃N— | 5 | 113 | 152 | 161 |
| 6 | HC≡C—CH₂— | piperidino (N—) | 1 | 109 | 123 | 133 |
| 8 | —CH₂—CH₂— (cyclic) | H, CH₃(CH₂)₃N— | 5 | 98 | 117 | 128 |
| 10 | (H₃C)₂C< | H, CH₃(CH₂)₃N— | 3 | 131 | 140 | 133 |
| 12 | CH₂< | pyrrolidino (N—) | 1 | 116 | 124 | 130 |
| 13 | CH₂< | morpholino (O⌐⌐N—) | 1 | 130 | 141 | 143 |
| 14 | CH₂< | 4-methylpiperazino (H₃C—N⌐⌐N—) | 1 | 122 | 143 | 130 |
| 15 | CH₂< | H, CH₃(CH₂)₃N— | 1 | 118 | 125 | 136 |
| 17 | CH₂< | cyclohexyl-NH— | 5 | 103 | 122 | 119 |
| 19 | CH₃CH< | piperidino (N—) | 5 | 106 | 133 | 125 |
| 20 | 3-pyridyl-CH₂— | piperidino (N—) | 1 | 124 | 150 | 145 |
| Compound 1 | CH₂< | piperidino (N—) | 1 | 121 | 142 | 140 |

TABLE 2-continued

Action on NGF production

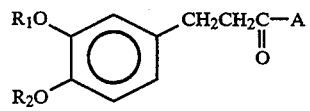

| Example No. | Structure R₁ and R₂ | A | Dose (mg/kg) | NGF increase (Control = 100) Striate body | Frontal lobe | Hippocampus |
|---|---|---|---|---|---|---|
| Compound 2 | CH₃— | 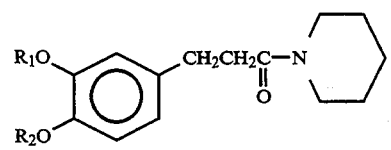 | 5 | 107 | 118 | 113 |

EXPERIMENTAL EXAMPLE 2

Measurement of Drug Concentration in Blood

Seven week old SPF Wister male rats (400–500 g body weight) were fasted overnight and divided into groups each consisting of 3 rats for the experiment. Administration was carried out forcibly using an oral probe at a rate of 20 mg/ml/kg body weight. Plasma samplings were carried out by bleeding whole blood from carotid arteries and jugular veins 20 minutes, 1 hour and 2 hours after the administration and centrifuging the blood in test tubes pre-treated with heparin before use. Measurements were made by using HPLC; peak areas were calculated from the calibration curve of the standard preparation.

The results with comparative compounds 1 and 2 are shown as follows:

| Compound | Structure | | Drug Concentration in blood (μg/ml) 20 min | 1 hr | 2 hr |
|---|---|---|---|---|---|
| 1 | 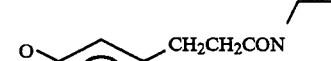 | Average SD | 2.73 1.85 | 0.59 0.07 | 0.07 0.04 |
| 2 | 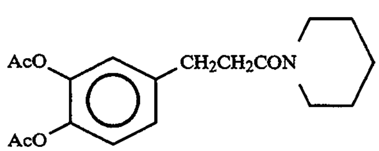 | Average SD | 1.02 0.52 | 0.23 0.08 | 0.02 — |

POSSIBLE INDUSTRIAL USE

Compounds according to the present invention can be used as agents for the prevention of the progression of degenerative diseases in the central nervous system and the therapeutic treatment thereof.

What is claimed is:

1. An amide derivative of dihydrocaffeic acid represented by the formula (I):

in which $R_1$ and $R_2$ are independently a propargyl, benzyl or pyridylmethyl group, or $R_1$ and $R_2$ are bound together to form a —CH₂CH₂— group; or a pharmacologically acceptable salt thereof.

2. A pharmaceutical composition containing together with a pharmaceutically acceptable carrier or diluent an effective amount of the compound of claim 1.

3. A method of inducing the production and secretion of nerve growth factor, comprising administering to a person in need thereof an amount of a compound of a formula

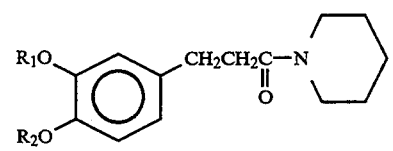

in which $R_1$ and $R_2$ are independently a propargyl, benzyl or pyridylmethyl group, or $R_1$ and $R_2$ are bound together to form a —CH₂CH₂— group or a pharmacologically acceptable salt thereof.

* * * * *